(12) United States Patent
Parker et al.

(10) Patent No.: US 9,709,470 B2
(45) Date of Patent: Jul. 18, 2017

(54) ON-DEMAND VAPOUR GENERATOR

(71) Applicant: Smiths Detection-Watford Limited, Bushey, Watford, Hertfordshire (GB)

(72) Inventors: Alexander Parker, Watford (GB); Marcel Gowers, Watford (GB); Jonathan Atkinson, Watford (GB); John Fitzgerald, Watford (GB)

(73) Assignee: Smiths Detection-Watford Limited, Hertfordshire (GB)

( * ) Notice: Subject to any disclaimer, the term of this patent is extended or adjusted under 35 U.S.C. 154(b) by 0 days.

(21) Appl. No.: 14/430,252

(22) PCT Filed: Sep. 24, 2013

(86) PCT No.: PCT/GB2013/052498
§ 371 (c)(1),
(2) Date: Apr. 30, 2015

(87) PCT Pub. No.: WO2014/045067
PCT Pub. Date: Mar. 27, 2014

(65) Prior Publication Data
US 2015/0247786 A1    Sep. 3, 2015

Related U.S. Application Data

(60) Provisional application No. 61/705,068, filed on Sep. 24, 2012.

(51) Int. Cl.
*H01J 49/00*    (2006.01)
*G01N 1/38*    (2006.01)
(Continued)

(52) U.S. Cl.
CPC .............. *G01N 1/38* (2013.01); *B01B 1/005* (2013.01); *B01D 53/229* (2013.01);
(Continued)

(58) Field of Classification Search
CPC ...... G01N 1/28; G01N 1/38; G01N 2001/381; H01J 49/00; H01J 49/02; H01J 49/04; H01J 49/0404; H01J 49/0422; H01J 49/0427
(Continued)

(56) References Cited

U.S. PATENT DOCUMENTS 5,471,979 A * 12/1995 Psaros ................. A61M 16/009
128/203.12
8,137,437 B2 * 3/2012 Atkinson ................ B01B 1/005
73/23.42
(Continued)

FOREIGN PATENT DOCUMENTS

CN    101583867 A    11/2009
CN    101939641 A    1/2011

OTHER PUBLICATIONS

International Search Report for PCT/GB2013/052498 dated Dec. 18, 2013.
(Continued)

*Primary Examiner* — Jason McCormack
(74) *Attorney, Agent, or Firm* — Advent, LLP

(57) ABSTRACT

An on-demand vapor generator includes a vapor chamber configured to produce a vapor and a vapor absorption assembly configured to receive flows of vapor from the vapor chamber. The vapor absorption assembly includes a first vapor-permeable passage having a passage outlet and at least one second vapor-permeable passage that is closed. When vapor absorption assembly receives a flow of vapor from the vapor chamber, the flow of vapor passes through the first vapor-permeable passage to the passage outlet at least substantially without absorption of vapor from the flow of vapor. However, when a flow of vapor is not received from the vapor chamber, vapor entering the vapor absorption assembly from the vapor chamber passes into the first
(Continued)

vapor-permeable passage and the at least one second vapor-permeable passage and is at least substantially absorbed.

10 Claims, 4 Drawing Sheets

(51) Int. Cl.
    *B01B 1/00*       (2006.01)
    *B01L 3/02*       (2006.01)
    *B01D 53/22*     (2006.01)
    *F22B 3/02*       (2006.01)
    *G01N 27/62*     (2006.01)

(52) U.S. Cl.
    CPC .............. *B01L 3/0289* (2013.01); *F22B 3/02* (2013.01); *G01N 27/622* (2013.01)

(58) Field of Classification Search
    USPC ........................................ 250/281, 282, 288
    See application file for complete search history.

(56) References Cited

U.S. PATENT DOCUMENTS

| | | | |
|---|---|---|---|
| 8,778,060 B2 * | 7/2014 | Atkinson | ................ B01B 1/005 250/282 |
| 2004/0099045 A1 | 5/2004 | Demarest et al. | |
| 2009/0133469 A1 * | 5/2009 | Atkinson | ................ B01B 1/005 73/23.42 |
| 2009/0166524 A1 | 7/2009 | Geraghty et al. | |
| 2010/0317125 A1 | 12/2010 | Taylor | |
| 2012/0175516 A1 | 7/2012 | Atkinson et al. | |

OTHER PUBLICATIONS

Official Action dated Mar. 18, 2016 for Chinese Appln. No. 201380049735.7.

* cited by examiner though not limited to these examples. It is further contemplated that on-demand vapour generators in accordance with the disclosure can be used in other applications and are not necessarily limited to use with a detector apparatus.

ON-DEMAND VAPOUR GENERATOR

BACKGROUND

Ion mobility spectrometry (IMS) refers to an analytical technique that can be used to separate and identify ionized material, such as molecules and atoms. Ionized material can be identified in the gas phase based on mobility in a carrier buffer gas. Thus, an ion mobility spectrometer (IMS) can identify material from a sample of interest by ionizing the material and measuring the time it takes the resulting ions to reach a detector. An ion's time of flight is associated with its ion mobility, which relates to the mass and geometry of the material that was ionized. The output of an IMS detector can be visually represented as a spectrum of peak height versus drift time.

IMS detectors and other detectors often include a vapour generator to supply a dopant chemical to the detector. Vapour generators can also be used to supply a test chemical for use in testing or calibrating a detector, a filter or other equipment. In some applications it is important that the vapour generator can be switched on and off rapidly, and that leakage can be prevented when the detector is switched off. For example, in an IMS detection system, rapid switching of the vapour generator on and off enables rapid switching between different doping conditions, such as different levels of dopant or different dopant substances. Such rapid switching could also enable different regions of the IMS detector to be doped differently by ensuring there was no leakage to undoped regions of the apparatus when the apparatus is switched off.

SUMMARY

An On-Demand Vapour Generator (OVG) is disclosed. The vapour generator may be configured for use with a detection apparatus, such vapour generators may comprise a vapour source coupled by a flow path to provide vapour through an impeder to an outlet for dispensing vapour to the detection apparatus. The impeder may comprise: a first vapour permeable passage arranged to impede diffusion of the vapour from the source to the outlet. The vapour permeable passage is configured to enable vapour to be driven through a diffusion barrier from the source to the outlet by a pressure difference (e.g. pumped or forced flow as opposed to simply a difference in concentration). The vapour generator may also comprise at least one additional vapour permeable passage to act as a sink, coupled to the outlet by the first vapour permeable passage. The sink can comprise a material adapted to take up the vapour to divert diffusion of vapour away from the outlet. In embodiments, the first vapour permeable passage and the sink are arranged so in response to a pressure difference between the outlet and the vapour source, resistance to driving vapour flow through the first vapour permeable passage to the outlet is less than the resistance to driving vapour flow into the sink. In one or more implementations, the vapour generator includes a vapour chamber configured to produce a vapour and a vapour absorption assembly configured to receive flows of vapour from the vapour chamber, for example via a diffusion barrier. The vapour absorption assembly includes a first vapour-permeable passage having a passage outlet. The vapour absorption assembly may further include one or more second vapour-permeable passages that are closed. When the vapour absorption assembly receives a flow (e.g. a pressure driven flow) of vapour from the vapour chamber, the flow of vapour passes through the first vapour-permeable passage to the passage outlet at least substantially without absorption of vapour from the flow of vapour. However, when a flow of vapour is not received from the vapour chamber, vapour entering the vapour absorption assembly from the vapour chamber passes into the first vapour-permeable passage and the at least one second vapour-permeable passage and is at least substantially absorbed.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Figure 1:
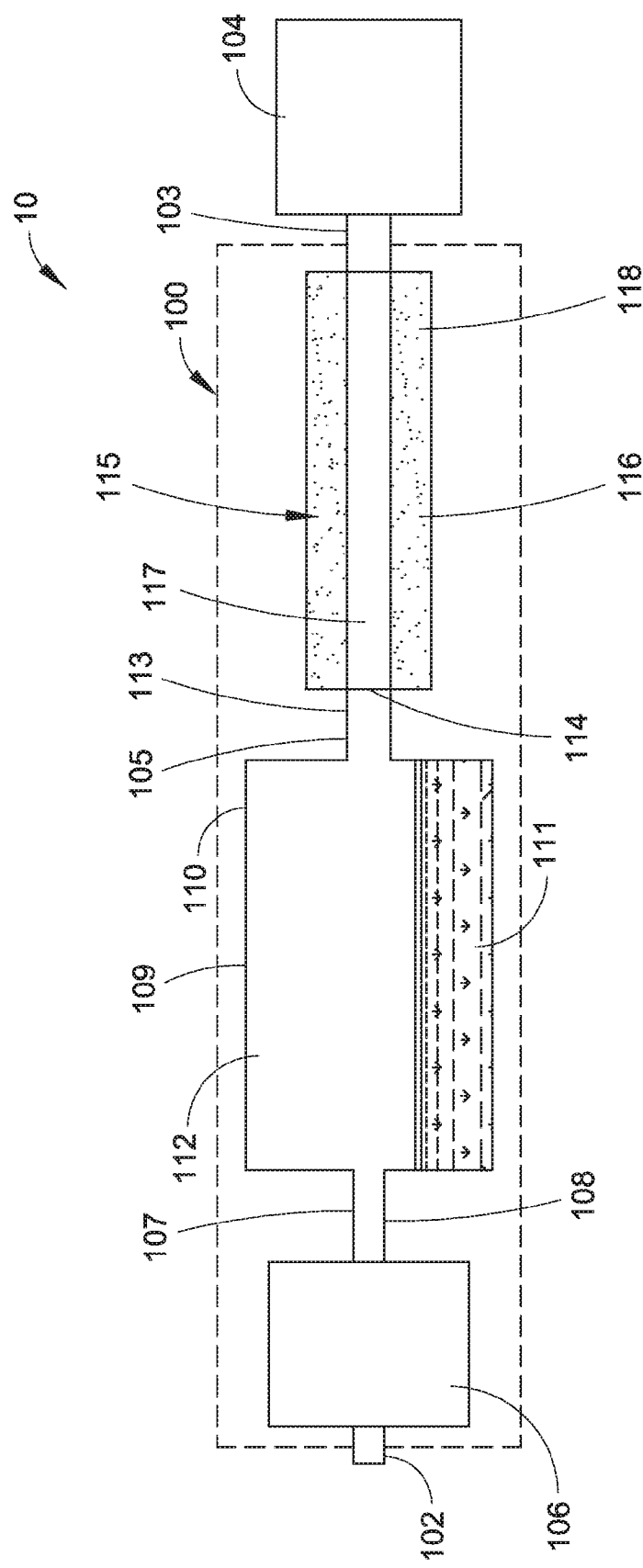
FIG. 1 is a schematic block diagram that illustrates an example on-demand vapour generator in accordance with an implementation of the disclosure, wherein the on-demand vapour generator employs a single vapour-permeable passage.

One technique of reducing leakage of vapour from a vapour generator when the vapour generator is turned off employs a container of absorbent material that is connected an outlet of a vapour generator via a T-junction. When the generator is turned on, the gas flow through the vapour generator rises to a level that is sufficient to ensure that most of the vapour is carried through the other arm of the T-junction to the outlet. When the vapour generator is off and there is a nominal (e.g., zero (0)) flow, some of the residual vapour produced passes via one arm of the T-junction to the absorbent material. However, some vapour may bypass the absorbent material leading to relatively low absorption efficiency and relatively high levels of escaped vapour.

An on-demand vapour generator is disclosed that is suitable for use in a detection system such as an IMS detection system, a gas chromatograph system, a mass spectrometer system, and so forth, to supply a flow of vapour to a detector apparatus (e.g., an IMS detector, a gas chromatograph, a mass spectrometer, and so forth) of the system.

In one or more implementations, the vapour generator includes a vapour chamber configured to produce a vapour. The vapour chamber includes a vapour chamber inlet configured to receive a flow of gas into the vapour chamber to generate a flow of vapour, and a vapour chamber outlet configured to allow the flow of vapour to exit the vapour chamber. A vapour absorption assembly receives flows of vapour from the vapour chamber and ports them to the detection apparatus (e.g., to an IMS detector). The vapour absorption assembly includes a vapour-absorbent material configured to absorb the vapour produced by the vapour chamber. A vapour-permeable passage having a passage outlet extends through the vapour-absorbent material and is coupled to the detector assembly. The vapour absorption assembly may further include at least one additional vapour-permeable passage that is closed (e.g., blocked so as to form a "dead end" vapour-permeable passage). When a flow of vapour is not driven (e.g. pumped or drawn) from the vapour chamber (e.g., the on-demand vapour generator is turned off so that there is negligible or no flow), any vapour entering the vapour absorption assembly from the vapour chamber passes into the vapour-permeable passage having the passage outlet and/or the one or more additional dead end vapour-permeable passages and is at least substantially absorbed by the vapour absorbing material. When the vapour absorption assembly receives a flow of vapour (e.g. when the flow of vapour is pumped or drawn) from the vapour chamber, the flow of vapour passes through the first vapour-permeable passage to the passage outlet. As the flow is driven through the passage, more vapour passes to the outlet without being absorbed than when the flow is not driven.

FIGS. 1 through 4 illustrate on-demand vapour generators 100 in accordance with example implementations of the present disclosure. As shown, the vapour generator 100 includes an inlet 102 and a vapour outlet 103 connected to an inlet of a detector apparatus 104. The vapour generator 100 is configured to furnish a readily controllable supply of a dopant vapour to the detector apparatus 104. In implementations, the vapour generator 100 may supply a flow of vapour to a variety of detector apparatus. For example, in one implementation, the detector apparatus 104 may comprise an IMS detector. However, the vapour generator 100 can be used in conjunction with other detectors such as gas chromatography instruments, and so forth. The vapour generator 100 may also be used for calibration purposes within the instrument. In implementations, the vapour generator 100 and detector apparatus 104 may be part of a detection system (e.g., an IMS detection system) 10. In such detection systems 10, the vapour generator 100 and the detector assembly can be housed within a common housing.

The vapour generator 100 includes a gas (e.g., air) flow generator 106 such as a fan, a blower, a compressed gas source, and so forth. The flow generator 106 is configured to be switched on or off to provide a flow of gas (air) to its outlet 107 as desired. The flow generator 106 may include various filters or other devices to remove contaminants and water vapour form the gas (e.g., from atmospheric air) before the gas is supplied to the outlet 107.

The outlet 107 of the flow generator 106 is in fluid communication with (e.g., is coupled to) an inlet 108 at one end of a vapour chamber 109. The vapour chamber 109 may have a variety of configurations, and may comprise any kind of vapour source, for example a permeation source, for example a diffusion source. For example, in the implementation shown, the vapour chamber 109 includes a housing 110 that contains a wicking, absorbent material 111 saturated with a compound in its liquid phase so that the space of the interior 112 within the housing 110 above the absorbent material 111 is at least substantially filled with a vapour of the liquid at the liquid's saturated vapour pressure at ambient temperature. The vapour chamber 109 includes an outlet 113 at the end opposite the inlet 108 through which a flow of vapour, comprised of the vapour and gas, can flow out of the vapour chamber 109. In implementations, the vapour producing liquid comprises acetone. However, vapour-producing substances other than acetone can be used.

The vapour chamber outlet 113 is in fluid communication with (e.g., is coupled to) an inlet 114 of a vapour absorption assembly 115, for example via a diffusion barrier. The vapour absorption assembly 115 includes a vapour absorbent 116 configured to absorb the vapour produced by the vapour chamber 109. A vapour-permeable passage (main flow path) 117 having an outlet (vapour outlet 103) extends through the vapour absorbent 116 and is coupled to the detector apparatus 104. In the illustrated implementations, the vapour absorption assembly 115 includes a single vapour-permeable passage 117. However, it is contemplated that additional vapour-permeable passages 117 may be provided in parallel to the passage 117 shown. Moreover, a second vapour absorption assembly can be provided between the inlet 108 of the vapour chamber 109 and the flow generator 106 to prevent vapour from the chamber 109 passing to the flow generator 106 in significant quantities when the flow of gas is off (e.g., when the flow generator 106 is turned off). A pneumatic valve can be connected between this second vapour absorption assembly and the vapour chamber. This valve may be maintained closed until gas (air) flow is required.

The on demand vapour generator 100 may further include one or more diffusion barriers 105. In implementations, the diffusion barriers may comprise flow paths with a small cross sectional area that limit the rate of diffusion (and therefore loss) of vapour from the vapour generator 100 when the generator 100 is in the off-state (e.g., when no flow of vapour is furnished by the vapour generator 100).

When the vapour generator 100 is off (e.g., is in the "off" state, that is, when no flow of vapour is provided), the flow generator 106 remains off so that there is no flow of gas (air) through the vapour chamber 109 and the vapour-permeable passage 117. The vapour-permeable passage 117 is open to the interior 112 of the vapour chamber 109 so that some vapour may drift into the passage 117. As this drift occurs, the vapour diffuses into the vapour-absorbent material and is absorbed therein. The bore, length, porosity and nature of the vapour absorbent 116 are chosen such that, under zero flow conditions (e.g., no or virtually no flow conditions), the amount of vapour that escapes from the outlet 103 end of the passage 117 is insignificant in the context of the application in which the vapour generator 100 is used. For example, where the vapour generator 100 is used as a dopant source in an IMS detector, the vapour dopant flow in the off state is arranged to be not sufficient to produce any noticeable dopant ion peak by the IMS detector.

The vapour generator 100 is turned on to produce a flow of vapour at its outlet 103 by turning on the flow generator 106 to produce a flow of gas (air) into the inlet 108 of the vapour chamber 109. This flow of gas (air) collects the vapour produced in the vapour chamber 109 and pushes it through the outlet 113 and into the passage 117 of the vapour absorption assembly 115. The flow velocity in the passage 117 is chosen such that the residence time of the collected vapour in the passage is sufficiently low so that little vapour is absorbed into the vapour absorbent 116. Thus, a greater proportion of the vapour passes through the vapour-permeable passage 117 to the outlet 103 end of the passage 117 to be delivered to the detector apparatus 104 than when the flow generator is off. The flow of vapour can be continuous or pulsed.

The vapour generator 100 is configured to be capable of turning off vapour flow very rapidly when not required, such that the vapour does not leak out at a significant rate. In an IMS detection system, this effectively prevents dopant vapour from entering the IMS detector when the system is turned off and is not powered. This can also enable selected regions of IMS detector to be doped with a reduced risk that dopant will leak to undoped regions when the apparatus is turned off. In conventional systems, gas flow through the IMS detector can keep undoped regions free of dopant when the apparatus is powered but, when not powered, the gas flow ceases and any slight leakage of dopant will contaminate all regions of the apparatus. This has previously made it very difficult to dope different regions of IMS detector differently except where the apparatus is continuously powered.

In FIGS. 1 through 4, the flow generator 106 is illustrated as being in fluid communication with (e.g., connected to) the inlet 102 of the vapour chamber 109 to push air into the chamber 109. However, in other implementations, the flow generator 106 may be connected downstream of the vapour chamber 109 and be arranged to pull air into the chamber 109. For example, the flow generator 106 may be connected between the outlet 113 of the vapour chamber 109 and the inlet 114 of the vapour absorption assembly 115 (the inlet 114 end of the vapour-permeable passage 117), or it could be connected downstream of the vapour absorption assembly 115 (at the outlet 103 end of the passage 117).

Figure 3:
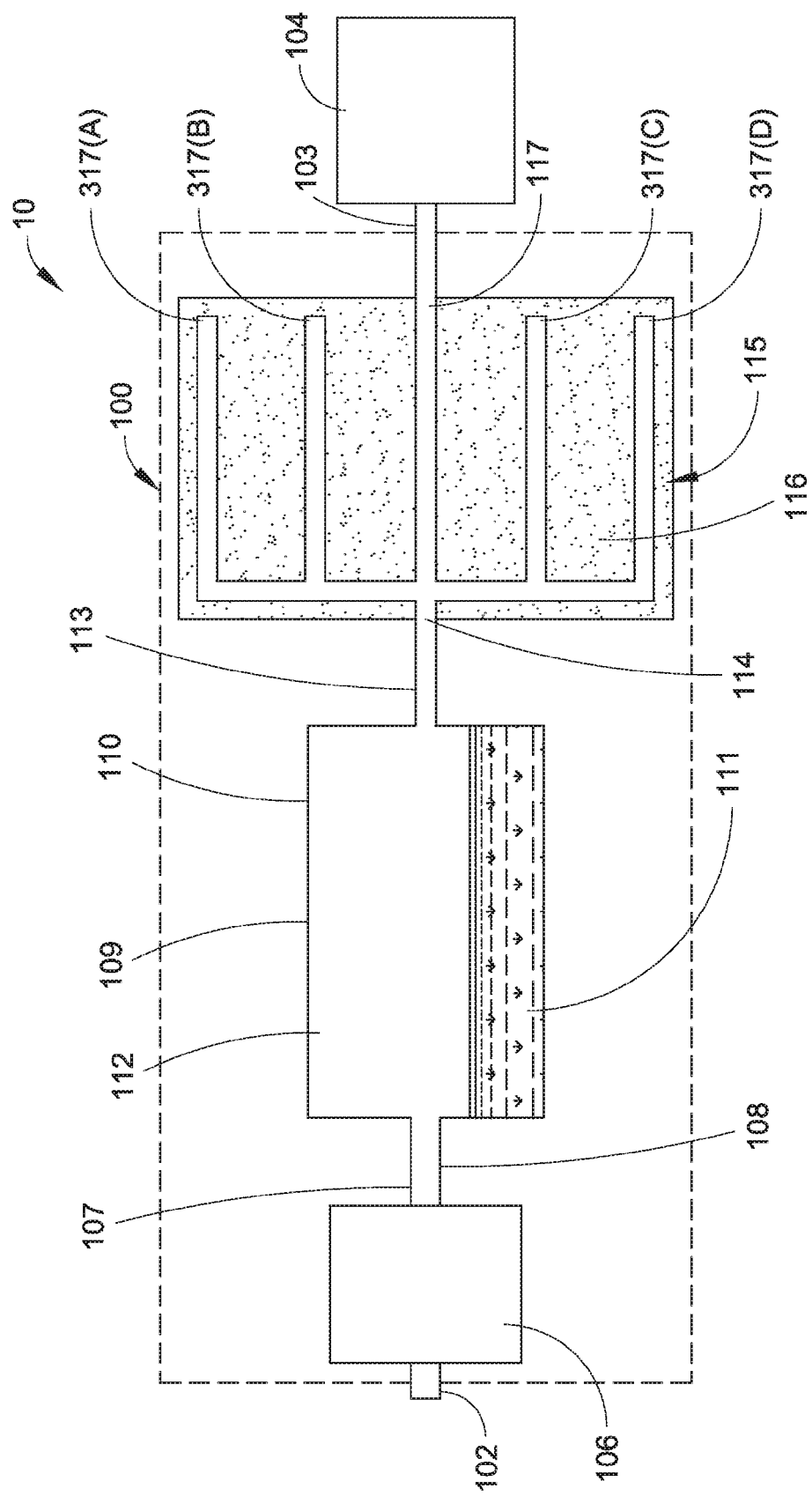
FIG. 3 is a schematic block diagram that illustrates an example on-demand vapour generator in accordance with an implementation of the disclosure, wherein the on-demand vapour generator employs a vapour-permeable passage having a passage outlet and one or more vapour-permeable passages that are closed.
Figure 4:
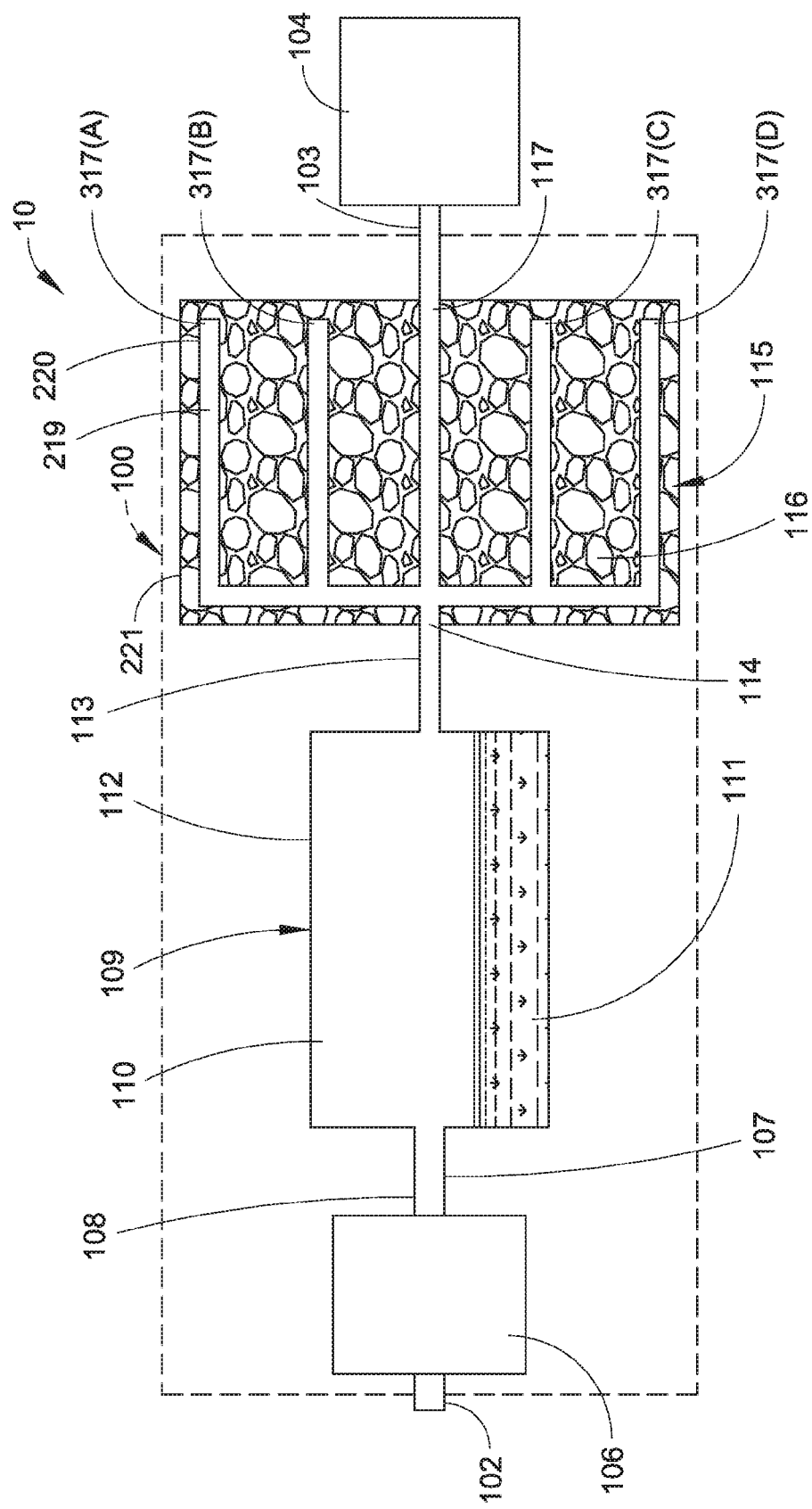
FIG. 4 is a schematic block diagram that illustrates an example on-demand vapour generator in accordance with another implementation of the disclosure, wherein the on-demand vapour generator employs a vapour-permeable passage having a passage outlet and one or more vapour-permeable passages that are closed.

In the implementations shown in FIGS. 3 and 4, the vapour absorption assembly 115 is illustrated as further including one or more additional vapour-permeable passages (region) that are closed (e.g., blocked) so as to form "dead end" vapour-permeable passages (four (4) dead end vapour-permeable passages 317A-D, collectively 317, are illustrated). As shown, the dead end vapour-permeable passages 317 may thus extend only partially through the vapour absorbent 116, and do not include outlets.

When the vapour absorption assembly 115 receives a flow of vapour from the vapour chamber 109 (e.g., the flow generator 106 is turn on), the flow of vapour passes through the primary vapour-permeable passage 117, which functions as a main flow path, to the passage outlet 103 at least substantially without absorption of vapour from the flow of vapour by the vapour absorbent 116. However, when a flow of vapour is not received from the vapour chamber (e.g., the flow generator 106 is turned off so that there is negligible or no flow of vapour), vapour entering the vapour absorption assembly 115 from the vapour chamber 109 passes into the vapour-permeable passage 117 and/or the dead end vapour-permeable passages 317 and is at least substantially absorbed by the vapour absorbent 116.

When the vapour generator 100 is in the off-state (e.g., when no flow of vapour is supplied), vapour diffusing out of the vapour chamber 109 enters the vapour absorption assembly 115 as before, but now passes down both the vapour-permeable passage 117 (main flow path) and the dead end vapour-permeable passages 317. As a result, the area of absorption provided for the vapour (and therefore the extent of absorption) is greatly increased. However, when the vapour generator 100 is in the on-state (e.g., when a flow of vapour is supplied), the dead end vapour-permeable passages 317 act as dead volumes with essentially no gas exchange and do not contribute to the absorption of vapour from the flow of vapour. Therefore, there is no significant change in the concentration of vapour exiting the vapour generator 100 with the the dead end vapour-permeable passages 317 from implementations that include only the vapour-permeable passage 117 without the dead end vapour-permeable passages 317.

In implementations, the addition of dead-end vapour-permeable passages 317 allows the width of the temperature range over which the on-demand vapour generator 100 can be operated to be increased. As temperature increases, the activity of permeation and diffusion sources rise, the rate of diffusion rises, and the ability of absorbent materials (e.g. activated charcoal) to capture chemicals often decreases. Consequently, a greater concentration of vapour, at a higher rate, is delivered to the vapour absorption assembly 115 of the vapour generator 100. This increase will be compounded by the reduction in absorption capacity/rate, leading to the vapour absorption assembly 115 being less capable of dealing with the vapour. Leakage in the off-state may therefore increase. Therefore, when the vapour-permeable passage 117 of the vapour absorption assemblies 115 shown in FIGS. 1 and 2 (without dead end vapour-permeable passages 317) are designed to be of suitable length to allow an adequate concentration of vapour to exit the vapour generator 100 in the on-state at extremely low temperatures, the passages 117 may not be adequately long to absorb all vapour in the off-state at extremely high temperatures. The addition of dead end vapour-permeable passages 317 to the vapour absorption assembly 115, as shown in FIGS. 3 and 4, increases the off-state absorption while not decreasing the on-state vapour concentration exiting the vapour generator 100. Accordingly, the addition of dead end vapour-permeable passages 317 to the vapour absorption assembly 115 makes it possible to reduce the leakage of vapour over a greater range of temperatures without limiting the ability of the vapour generator 100 to supply adequate vapour at extremely low temperatures. Moreover, the additions of dead end vapour-permeable passages 317 makes it possible to further increase the concentration of the vapour leaving the vapour generator 100 without compromising the ability of the vapour generator 100 to restrict the leakage of vapour in the off-state.

In implementations, addition of dead end vapour-permeable passages 317 to the vapour absorption assembly 115, as shown in FIGS. 3 and 4, may facilitate shortening of the main flow path (e.g., shortening of the vapour-permeable passage 117) to allow higher vapour concentrations to be produced by the vapour generator 100 in the on-state without limiting the ability of the generator 100 to limit leakage in the off-state. Moreover, in situations where the detection system 10 is to be operated over a range of temperatures, the addition of dead end vapour-permeable passages 317 to the vapour absorption assembly 115 enhances the ability of the vapour generator 100 to furnish an adequate concentration of vapour exiting the vapour generator 100 in the on-state at low temperature by having a short main flow path (when the activity of the source is lower than at high temperature), while simultaneously restricting the leakage of the vapour generator 100 in the off-state to acceptable levels at higher temperatures (when the activity of the source and the rate of diffusion are higher than at low temperatures).

The dimensions, layout and configuration of the vapour absorption assemblies 115 of the on-demand vapour generators 100 shown in FIGS. 1 through 4, including the the vapour-permeable passage 117 (main flow path) and/or the dead end vapour-permeable passages 317 may vary depending on a variety of factors including, but not limited to: the activity of the vapour source (vapour chamber 109), the required concentrations to be provided, the flows used in the on-state of the vapour generator 100, the acceptable level of release when in the off-state and the conditions (e.g. temperature) under which the vapour generator 100 be operated. Accordingly, any dimensions, layouts, or configurations presented herein are for illustrative purposes, and are not necessarily meant to be restrictive of the disclosure.

In implementations shown in FIGS. 1 and 3, the vapour-permeable passage 117 and/or the dead end vapour-permeable passages 317 of the vapour absorption assembly 115 comprise machined bores formed in a block 118 of an absorbent material such as carbon (e.g., activated charcoal) or a sintered material, such as a molecular sieve material, which could be of zeolite. In other implementations, the vapour-permeable passage 117 and dead end vapour-permeable passages 317 may be formed by molding the block 118 about a core structure that is subsequently removed. The absorbent material is configured to be absorbent of the vapour (e.g., of acetone vapour, and so forth). For example, the material may itself be formed of an absorbent material, such as carbon (e.g., activated charcoal), or the material itself may be a non-absorbent material rendered absorbent via impregnation with a suitable substance. In this manner, the vapour (e.g., acetone vapour, and so forth) may be absorbed by the vapour absorbent 116 generally along the length of the vapour-permeable passage 117 and within the dead-end vapour-permeable passages.

Figure 2:
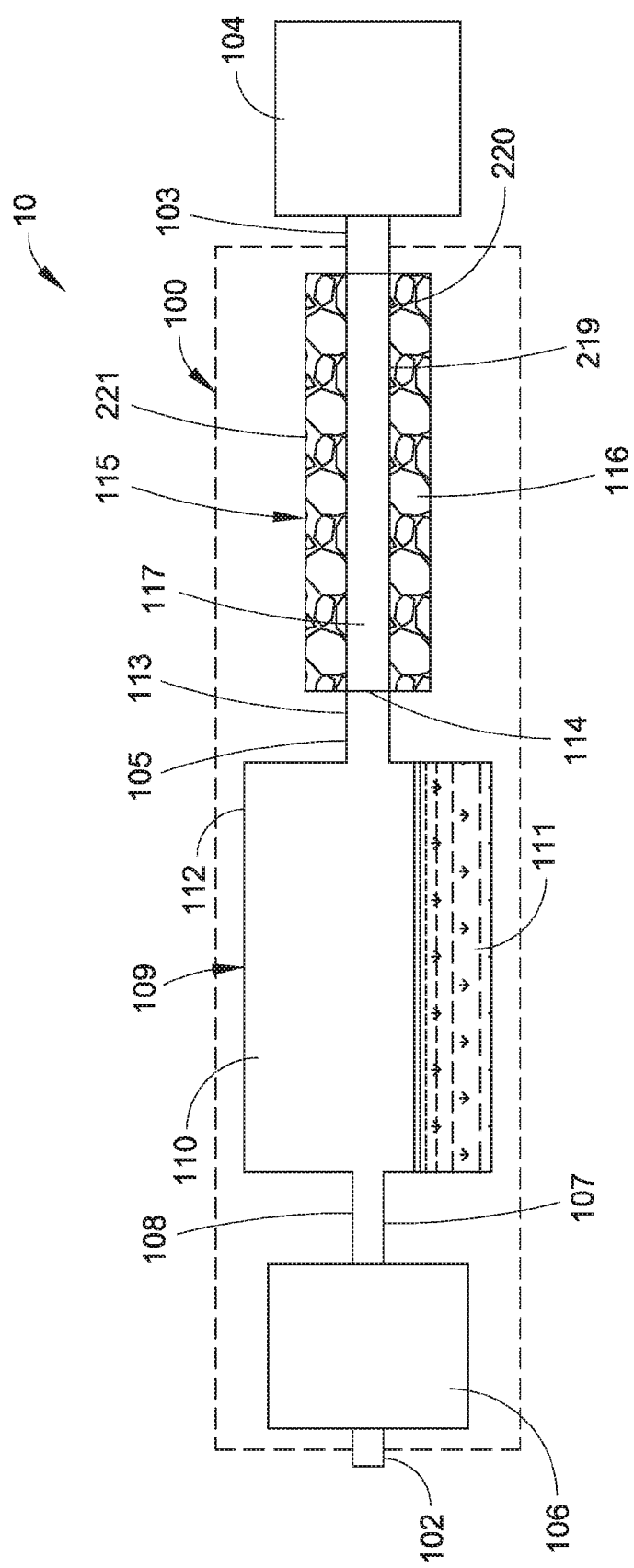
FIG. 2 is a schematic block diagram that illustrates another example on-demand vapour generator in accordance with an implementation of the disclosure, wherein the on-demand vapour generator employs a single vapour-permeable passage.

In the implementation shown in FIGS. 2 and 4, the vapour-permeable passage 117 and/or the dead end vapour-permeable passages 317 comprise lengths of tube 219 having a vapour-permeable outer wall or membrane 220 that are at least substantially enclosed within an outer housing 221 formed of a vapour-impermeable material. For example, as shown, the tube 219 forming the vapour-permeable passage 117 may extend axially along the center of the housing 221, while tubes 219 forming the dead end vapour-permeable passages 317 are arrayed around the central tube. As shown, the tube 219 that forms the vapour-permeable passage 117 includes a first end coupled to the inlet 114 and a second end coupled to the vapour outlet 103. Similarly, the tubes that form the dead end vapour-permeable passages 317 include first ends that are coupled to the inlet 114. However, the second ends of these tubes are blocked and do not extend from the housing 221. The bore, length, wall thickness and material of the tubes 219 may be chosen such that, under zero flow conditions, the amount of vapour that escapes from the outlet 103 end of the tube 219 is insignificant in the context of the application in which the vapour generator 100 is employed. In one example, the tube 219 forming the vapour-permeable passage 117 shown in FIG. 2 is approximately one hundred millimeters (100 mm) long with an external diameter of approximately one millimeter (1 mm), and an internal diameter of approximately one half millimeter (0.5 mm). However, tubes 219 having other sizes are contemplated. The volume between the outside surface of the tubes 219 and the inside surface of the housing 221 is at least substantially filled with a material 221 that readily absorbs the vapour produced by the vapour chamber 109. In implementations, the material 221 may comprise activated charcoal granules that are effective to absorb vapour, such as acetone vapour, or the like. Thus, the tubes 219 may be surrounded on all sides by the absorbent charcoal granules. In implementations, the tubes 219 may be formed of an elastomeric plastic, such as silicone rubber, and so forth.

In implementations, the on-demand vapour generator 100 may further include a pneumatic valve connected to block flow of vapour from the vapour chamber 109 to the absorbent passage until vapour flow is employed. The pneumatic valve would have the advantage of preventing continual adsorption of the vapour into the vapour absorbent 116, thus lengthening the life of both the vapour chamber 109 and the absorbent material of the vapour absorbent 116. The vapour-permeable passage 117 and/or the dead end vapour-permeable passages 317 may thus trap vapour that permeates through the valve seals, providing a lower rate of diffusion. Consequently, the size of the vapour absorbent assembly 115 (e.g., the length, surface area, etc. of the vapour-permeable passage 117 and/or the dead end vapour-permeable passages 317) may be reduced.

In FIGS. 1 through 4, the vapour absorbent 116 is illustrated as extending around the vapour-permeable passage 117 and/or the dead end vapour-permeable passages 317. However, in implementations, the entire vapour generator 100 may be at least substantially enclosed in a vapour absorbent so that vapour does not substantially escape from the vapour generator 100 in the off state.

The on-demand vapour generator 100 of the present disclosure provides for efficient trapping of vapour. The vapour generator 100 is not confined to use in doping detectors but could be used in other applications. For example, the vapour generator 100 may be used to provide a periodic internal calibrant material in a detection system 10. The detection system 10 may be an IMS detection system, gas chromatograph system, a mass spectrometer or other system. The vapour generator 100 may be used for calibration or testing of other detectors, filters, and so forth.

As will be appreciated in the context of the present disclosure, the vapour generator need not generate new vapour, it may generate pre-existing vapour obtained from a vapour source, e.g. a reservoir of vapour. As will also be appreciated in the context of the present disclosure, the term "absorption" need not imply chemical or molecular action, and may be taken to comprise at least one of adsorbing the vapour onto a surface, chemical absorption, take up of the vapour by chemical or molecular action, and at least temporary capture of the vapour in a porous material. As will also be appreciated, the volume flow rate along a flow passage may depend on the length and cross section of the flow passage, and the pressure difference applied to drive flow along the passage. Accordingly, a vapour permeable passage provides an example of a flow impeder in that the volume flow rate along the passage is impeded by the finite cross section and finite width of the passage. Flow may also be impeded by other examples of flow impeders such as any means of inhibiting flow, for example by slowing flow by means of adsorption, absorption, or by interposing a barrier in the flow.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components, and so forth can be constructed in a variety of ways without departing from this disclosure. Rather, the specific features and acts are disclosed as example forms of implementing the claims.

What is claimed is:

1. A vapour generator comprising:

a vapour chamber configured to produce a vapour; and a vapour absorption assembly including a sink and a first vapour-permeable passage having a passage outlet, the sink separated from the outlet by the first vapour permeable passage, the sink including a material configured to take up the vapour, the vapour absorption assembly configured to receive flows of vapour from the vapour chamber, wherein when a flow of vapour is received, the flow of vapour passes through the first vapour-permeable passage to the passage outlet at least substantially without absorption of vapour from the flow of vapour, and when a flow of vapour is not received from the vapour chamber, vapour entering the vapour absorption assembly from the vapour chamber passes into the first vapour-permeable passage and is diverted by diffusion away from the outlet by the sink, the sink including a dead end vapour-permeable passage, the dead end vapour permeable passage extending at least partially though the material configured to take up the vapour so that when a flow of vapour is received, the dead end vapour permeable passage comprises a dead volume that does not substantially contribute to absorption of vapour from the flow of vapour.

2. The vapour generator as recited in claim 1, wherein at least one of the first vapour-permeable passage or the sink comprises vapour-permeable tubing.

3. The vapour generator as recited in claim 2, wherein the tubing comprises an elastomer.

4. The vapour generator as recited in claim 1, further comprising a vapour-absorbent material, at least one of the first vapour-permeable passage or the sink at least partially extending through the vapour-absorbent material so that the vapour is absorbed by the vapour-absorbent material.

5. The vapour generator as recited in claim 1, wherein the vapour-absorbent material comprises carbon.

6. A vapour absorption assembly for a vapour generator, the vapour absorbent assembly comprising:

a vapour-absorbent material configured to absorb a vapour;

a first vapour-permeable passage extending though the vapour-absorbent material, the first passage having a passage outlet; and at least one second vapour-permeable passage extending at least partially through the vapour-absorbent material so that the at least one second passage is closed at a dead end, wherein when a flow of vapour is received, the second vapour permeable passage comprises a dead volume that does not substantially contribute to absorption of vapour from the flow of vapour and the flow of vapour passes through the first vapour-permeable passage to the passage outlet at least substantially without absorption of vapour from the flow of vapour by the vapour-absorbent material, and when a flow of vapour is not received, vapour entering the vapour absorption assembly passes into the first vapour-permeable passage and the second vapour permeable passage and is at least substantially absorbed.

7. A detection system comprising:

a detection apparatus, and a vapour generator comprising:

a vapour chamber configured to produce a vapour, the vapour chamber including a vapour chamber inlet configured to receive a flow of gas into the vapour chamber to generate a flow of vapour and a vapour chamber outlet configured to allow the flow of vapour to exit the vapour chamber; and a vapour absorption assembly configured to receive a flow of vapour from the vapour chamber outlet, the vapour absorption assembly including:

a vapour-absorbent material configured to absorb the vapour produced by the vapour chamber;

a first vapour-permeable passage extending though the vapour-absorbent material, the first vapour-permeable passage having a passage outlet configured to pass the flow of vapour to the detection apparatus; and at least one second vapour-permeable passage extending at least partially through the vapour-absorbent material so that the at least one second vapour-permeable passage is closed at a dead end, wherein when a flow of vapour is received from the vapour chamber outlet, the second vapour permeable passage comprises a dead volume that does not substantially contribute to absorption of vapour from the flow of vapour and the flow of vapour passes through the first vapour-permeable passage to the passage outlet at least substantially without absorption of vapour from the flow of vapour by the vapour-absorbent material, and when a flow of vapour is not received from the vapour chamber, vapour entering the vapour-absorbent passage assembly from the vapour chamber passes into the first vapour-permeable passage and the at least one second vapour-permeable passage and is at least substantially absorbed by the vapour-absorbent material.

8. The detection system as recited in claim 7, wherein at least one of the first vapour-permeable passage or the at least one second vapour-permeable passage comprises vapour-permeable tubing.

9. The detection system as recited in claim 7, further comprising a passage inlet configured to receive flows of vapour from the vapour chamber outlet, the first vapour-permeable passage having a first end in fluid communication with the passage inlet and a second end in fluid communication with the passage outlet, and the at least one second vapour-permeable passage having a first end in fluid communication with the passage inlet and a second end that is sealed.

10. The detection system as recited in claim 7, wherein the detection apparatus comprises an ion mobility spectrometry (IMS) detector.

* * * * *